United States Patent [19]

Mettler et al.

[11] Patent Number: 5,149,870
[45] Date of Patent: Sep. 22, 1992

[54] PROCESS FOR THE PRODUCTION OF 1-(AMINOMETHYL)CYCLOHEXANE ACETIC ACID

[75] Inventors: Hans P. Mettler, Brig-Glis; Felix Previdoli, Brig, both of Switzerland

[73] Assignee: Lonza Ltd., Gampel/Valais, Switzerland

[21] Appl. No.: 786,721

[22] Filed: Nov. 1, 1991

Related U.S. Application Data

[62] Division of Ser. No. 612,985, Nov. 15, 1990, and Ser. No. 727,939, Jul. 10, 1991, Pat. No. 5,095,148.

[30] Foreign Application Priority Data

Nov. 16, 1989 [CH] Switzerland ............ 4128/89

[51] Int. Cl.$^5$ ............................................. C07C 61/08
[52] U.S. Cl. .................................................. 562/507
[58] Field of Search ...................................... 562/507

[56] References Cited

U.S. PATENT DOCUMENTS

| | | |
|---|---|---|
| 4,024,175 | 5/1977 | Satzinger et al. ............... 260/468 |
| 4,152,326 | 5/1979 | Hartenstein et al. ............ 546/16 |
| 4,956,473 | 9/1990 | Mettler et al. ................... 548/408 |
| 4,958,044 | 9/1990 | Mettler et al. ................... 558/431 |

OTHER PUBLICATIONS

Krapcho et al., Synthesis, (1982), 805–821; pp. 893–914.
New et al., Synthesis (1983), pp. 388 to 389.
Drugs of the Future, vol. 9, No. 6, (1984), pp. 418 and 419.
Aneya et al., Tetrahedron Letters, vol. 24, No. 23, (1983), pp. 4641 to 4644.

Primary Examiner—Michael L. Shippen
Attorney, Agent, or Firm—Fisher, Christen & Sabol

[57] ABSTRACT

A new process is described for the production of 1-(aminomethyl)cyclohexane acetic acid, a pharmaceutical agent used as an anticonvulsant. For this purpose a (1-cyanocyclohexyl)malonic acid dialkyl ester is decarbalkoxylated to the corresponding (1-cyanocyclohexyl)acetic acid alkyl ester, then transesterified with a benzyl alcohol and finally hydrogenated to form the end product.

14 Claims, No Drawings

PROCESS FOR THE PRODUCTION OF 1-(AMINOMETHYL)CYCLOHEXANE ACETIC ACID

This is a divisional of U.S. Ser. No. 612,985, pending filed on Nov. 15, 1990, and a divisional of U.S. Ser. No. 727,939, filed on Jul. 10, 1991, now U.S. Pat. No. 5,095,148.

BACKGROUND OF THE INVENTION

1. Field Of The Invention

The invention relates to a new process for the production of 1(aminomethyl)cyclohexane acetic acid as well as to (1-cyanocyclohexyl)acetic acid ester as new intermediate products in the process according to the invention.

2. Description of Related Art 1-(Aminomethyl)cyclohexane acetic acid is used under the name Gabapentin in medicine as an anticonvulsant. Gabapentin, its use and production are described in *Drugs of the Future*, Vol. 9, No. 6, 1984, pp. 418 to 419, as well as in U.S. Pat. Nos. 4,024,175 and 4,152,326, which are hereby incorporated by reference in their entireties. Production of Gabapentin under these known methods is very expensive, however, and includes seven to eight technically difficult and error-prone steps.

SUMMARY OF THE INVENTION

Therefore the object was to find a process that excludes said drawbacks.

This object was able to be obtained with a process for the production of 1-(aminomethyl)cyclohexane acetic acid of the formula:

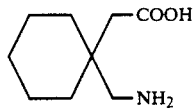

(I)

The process is characterized in that in a first step a (1-cyanocyclohexyl) malonic acid dialkyl ester of the general formula:

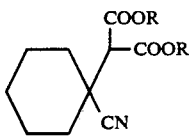

(II)

in which R is an alkyl with 1 to 4 carbon atoms, is decarbalkoxylated to the corresponding (1-cyanocyclohexyl)acetic acid alkyl ester of the general formula:

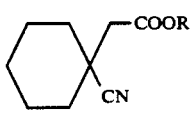

(III)

in which R is defined as above. In a second step, the alkyl ester is transesterified with a benzyl alcohol of the general formula:

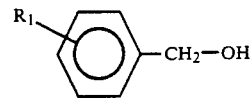

(IV)

i.e., in which $R_1$ is H, an alkoxy group, a nitro group or a halogen, in the presence of a basic catalyst to form a (1-cyanocyclohexyl)acetic acid benzyl ester of the general formula:

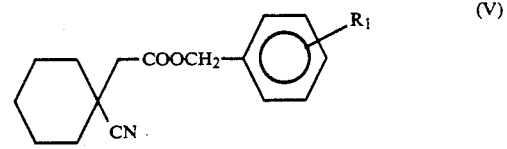

(V)

in which $R_1$ is defined as above. Finally the benzyl ester is hydrogented in the presence of a hydrogenating catalyst to form the end product with hydrogen.

DESCRIPTION OF THE PREFERRED EMBODIMENTS

The initial products in the process according to the invention are (1-cyanocyclohexyl)malonic acid dialkyl esters of the general formula:

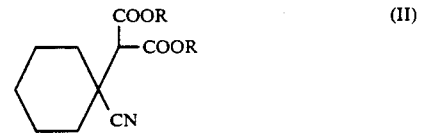

(II)

in which R means an alkyl with 1 to 4 carbon atoms. These compounds are described in Swiss Patent Application CH 3127/88, which is hereby incorporated by reference in its entirety, and are accessible in a simple way from cyclohexanone.

The methyl or ethyl esters preferably are used for the process according to the invention.

In the first process step, the initial product is decarbalkoxylated to a (1-cyanocyclohexyl)acetic acid alkyl ester of the general formula:

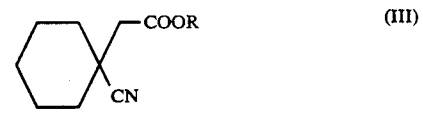

(III)

in which R means an alkyl with 1 to 4 carbon atoms. These compounds have not been described up to now.

The decarbalkoxylation can be performed according to methods known in the literature, e.g., according to Krapcho et al., *Synthesis* 1982, pages 805 to 921 and 893 to 914, or according to Aneya et al., *Tetrahedron Letters* 1983, Vol. 24, No. 43, pages 4641 to 4644, which are hereby incorporated by reference in their entirety.

Then suitably the operation is performed in boric anhydride or in dipolar aprotic solvents such as dimethyl sulfoxide, in combination with water as reaction medium at temperature between 100° and 250° C. Optionally the reaction can be performed in the presence of alkali or alkaline-earth salts, such as alkali or alkaline-earth chlorides, cyanides or acetates.

The resulting (1-cyanocyclohexyl)acetic acid alkyl ester is suitably isolated and purified by distillation.

Alternatively, it is also possible to produce the (1-cyanocyclohexyl)acetic acid alkyl esters by alcoholysis of (1-cyanocyclohexyl)acetonitrile of the general formula:

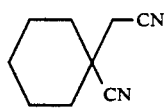
(VI)

with a lower aliphatic alcohol in the presence of a mineral acid and then hydrolyzing the mixture with water.

In this case, the (1-cyanocyclohexyl)acetonitrile is accessible according to New et al., *Synthesis* 1983, pages 388 and 389, which is hereby incorporated by reference in its entirety, from the corresponding cyclohexylidene malonic acid ester.

The alcoholysis is performed with a lower alcohol, preferably with methanol or ethanol, in the presence of a mineral acid from the series hydrogen chloride, hydrogen bromide or anhydrous sulfuric acid.

Both the alcohol and the mineral acid are suitably used in amounts of 1 to 100 equivalents relative to the nitrile.

The reaction temperature is suitably between −20° and 50° C., the pressure between 1 and 10 bars.

Optionally, an additional aprotic solvent, such as, e.g., an aliphatic or aromatic hydrocarbon, an ether, ester, or a halogenated hydrocarbon can be used as reactant together with the alcohol.

The intermediate product (Imidat) occurring in the alcoholysis is not isolated but is directly hydrolyzed with water, preferably in excess, at temperatures between −20° and 100° C. to form the (1-cyanocyclohexyl)acetic acid alkyl ester.

In the subsequent step, the alkyl ester is transesterified with a benzyl alcohol of the general formula:

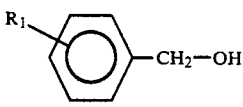
(IV)

in which $R_1$ means H or an alkoxy group, a nitro group or a halogen in the presence of a catalyst to form a (1-cyanocyclohexyl)acetic acid benzyl ester of the general formula:

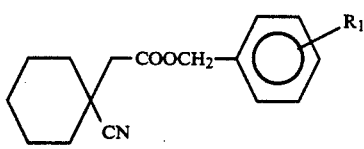
(V)

in which $R_1$ means H or an alkoxy group, a nitro group or a halogen.

These compounds have not been described up to now.

The transesterification is preferably performed with benzyl alcohol in the presence of a base as catalyst.

Suitable bases are the cyanides such as, e.g., potassium cyanide, alcoholates such as, e.g., sodium methylate or potassium tert-butylate or tertiary amines such as, e.g., triethylamine or N,N-dimethylaminopyridine.

The catalyst is suitably used in amounts between 0.01 and mol percent, preferably between 0.2 and 3 mol percent.

Advantageously, the operation is performed in the presence of an aprotic solvent, such as dimethyl ether or tetrahydrofuran, or an aromatic or aliphatic hydrocarbon, such as toluene or hexane.

The reaction temperature for the transesterification is suitably between 0° C. and the boiling point of the benzyl alcohol used.

The reaction product is suitably isolated and purified by distillation.

Alternatively, the (1-cyanocyclohexyl)acetic acid benzyl ester may also be produced by alcoholysis of (1-cyanocyclohexyl)acetonitrile of the general formula:

(VI)

with a benzyl alcohol of the general formula:

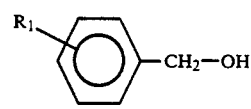
(IV)

in which $R_1$ means H or an alkoxy group, a nitro group or halogen, preferably benzyl alcohol, in the presence of a mineral acid, preferably from the series hydrogen chloride, hydrogen bromide or anhydrous sulfuric acid.

Both the benzyl alcohol and the mineral acid are suitably used in amounts from 1 to 100 equivalents, relative to the nitrile.

The reaction temperature is suitably between −20° and 50° C., the pressure is suitably between 1 and 10 bars.

Optionally an additional aprotic solvent, such as, e.g., an aliphatic or aromatic hydrocarbon, an ether, ester, or a halogenated hydrocarbon can be used as reactant together with the alcohol.

The intermediate product (Imidat) occurring in the alcoholysis is not isolated but is directly hydrolyzed with water, preferably in excess, at temperatures between −20° and 100° C. to form the (1-cyanocyclohexyl)acetic acid benzyl ester.

In the last step, the catalytic hydrogenation of the benzyl ester with hydrogen to the desired end product, 1(aminomethyl)cyclohexane acetic acid, takes place.

Noble metal catalysts such as platinum, palladium, rhodium, ruthenium catalysts, optionally applied to inert supports such as activated carbon or aluminum oxide or Raney catalysts such as, e.g., Raney nickel or Raney cobalt catalysts, or (noble) metal oxides, such as, e.g., nickel oxide or platinum oxide can be used as a hydrogenating catalyst.

Suitably, the amount of catalyst varies between 1 and 50 percent by weight, relative to the benzyl ester used.

Advantageously, the benzyl ester is hydrogenated in the presence of a suitable solvent, such as a lower alcohol, e.g., ethanol, methanol; a carboxylic acid, e.g., acetic acid; an ester, e.g., ethyl acetate; or an ether or alcohol in combination with ammonia.

The pressure suitably varies in the range of 1 to 100 bars, preferably between 2 and 10 bars, the temperature suitably varies between 0° and 100° C. The optimal temperature is largely dependent on the catalyst used.

The desired product already precipitates in great purity, but optionally can be further purified by recrystallization.

EXAMPLE 1

Production of (1-cyanocyclohexyl)acetic acid ethyl ester 26.9 g (100 mmol) of (1-cyanocyclohexyl)malonic acid dimethyl ester, 4.3 g (100 mmol) or lithium chloride and 3.6 g (200 mmol) of water were heated in 300 ml of dimethyl sulfoxide for 22 hours to 150° C. Then it was cooled, mixed with 700 ml of water and extracted with 1000 ml of pentane. 14.4 g of (1-cyanocyclohexyl)acetic acid ethyl ester was obtained by distillation of the organic phase, corresponding to a yield of 74 percent (relative to the (1-cyanocyclohexyl)malonic acid dimethyl ester used). Data for the product was:

Boiling point: 125°–130° C./2–4 mbars

Elementary analysis for $C_{11}H_{17}NO_2$ (195.3): Cld: C, 67.7%; H, 8.8%; N, 7.2%. Fnd: C, 67.7%; H, 8.7%; N, 7.0%.

$^1$H-NMR: (DMSO-D$_6$, 300 MHz) δ: 1.20 (t, 3H) 1.10–1.25 (m, 1H) 1.34–1.56 (m, 4H) 1.61–1.77 (m, 3H) 1.93–2.03 (m, 2H) 2.69 (s, 2H) 4.11 (q, 2H)

EXAMPLE 2

Production of (1-cyanocyclohexyl)acetic acid benzyl ester 401 mg (2 mmol) of (1-cyanocyclohexyl)acetic acid ethyl ester, 1.09 g (10 mmol) of benzyl alcohol and 6 mg (0.1 mmol) of potassium cyanide were refluxed for 24 hours in 5 ml of toluene. Then the solution was washed with 25 ml of water, freed of solvent and distilled in high vacuum. 350 mg of (1-cyanocyclohexyl)acetic acid benzyl ester was obtained, corresponding to a yield of 68 percent (relative to the (1-cyanocyclohexyl)acetic acid ethyl ester used). Data for the product was:

Boiling point: 148°–152° C./0.1–02 mbar

Elementary analysis for $C_{16}H_{19}NO_2$ (257.3): Cld: C, 74.7%; H, 7.4%; N, 5.4%. Fnd: C, 74.9%; H, 7.4%; N, 5.5%.

$^1$H-NMR: (CDCL$_3$, 300 MHz) δ 1.13–1.27 (m, 1H) 1.28–1.42 (m, 2H) 1.59–1.80 (m, 5H) 2.04–2.12 (m, 2H) 2.59 (s, 2H) 5.12 (s, 2H) 7.30–7.41 (m, 5H)

EXAMPLE 3

Production of 1-(aminomethyl)cyclohexane acetic acid 1.0 g (3.8 mmol) of (1-cyanocyclohexyl)acetic acid benzyl ester was distilled in 20 ml of methanol, mixed with 0.2 g of Rh/C 5 percent and hydrogenated at 10 bars of hydrogen pressure. After 23 hours at room temperature the suspension was filtered, the filtrate was concentrated to 3 ml, mixed with 25 ml of ethanol, concentrated to 4 ml and put on the cooling shelf. The precipitated product was filtered, washed with ethanol and dried. 0.18 g of Gabapentin was obtained, corresponding to a yield of 27 percent (relative to the (1-cyanocyclohexyl)acetic acid benzyl ester used). Data for the produce was:

Melting point: 148°–151° C.

$^1$H-NMR: (CD$_3$OD, 300 MHz) δ: 1.30–1.67 (m, 10H) 2.47 (s, 2H) 2.89 (s, 2H)

EXAMPLE 4

Production of (1-cyanocyclohexyl)acetic acid benzyl ester from (1-cyanocyclohexyl)acetonitrile 1.52 g (10 mmol) of (1-cyanocyclohexyl)acetonitrile and 13.1 g (120 mmol) of benzyl alcohol were saturated in 20 ml of toluene at 0° C. with HCl gas. After 22 hours, it was mixed with 25 ml of water and 100 ml of dimethyl ester, stirred well for 30 minutes and filtered. The organic phase was separated and concentrated by evaporation. 13 g of product was obtained, which according to gas chromatography contained 2.22 percent of (1-cyanocyclohexyl)acetic acid benzyl ester, corresponding to a yield of 11 percent (relative to the (1-cyanocyclohexyl)acetonitrile used).

EXAMPLE 5

Production of (1-cyanocyclohexyl)acetic acid ethyl ester from (1-cyanocyclohexyl)acetonitrile (1-Cyanocyclohexyl)acetonitrile (7.60 g, 50 mmol) was suspended in 30 ml of ethanol and saturated (3 bars) with HCl gas in the autoclave at 0° C. After 22 hours it was expanded, evacuated (18 mbars) in 30 minutes, mixed with 150 ml of water and stirred for 3 hours at 10° C. Then it was concentrated on the rotary evaporator to 168 g and extracted with 50 ml of ethyl acetate. 4.04 g of (1-cyanocyclohexyl)acetic acid ethyl ester was able to be isolated from the organic phase by distillation, corresponding to a yield of 41 percent (relative to the (1-cyanocyclohexyl)acetonitrile used).

What is claimed is:

1. Process for the production of 1-(aminomethyl)cyclohexane acetic acid of the formula:

(I)

comprising:

(a) reacting (1-cyanocyclohexyl)acetonitrile of the formula:

(VI)

with a benzyl alcohol of the general formula:

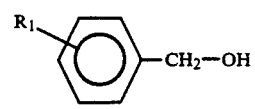

(IV)

wherein $R_1$ is H, an alkoxy group, a nitro group or halogen, in the presence of a mineral acid, and subsequently the reaction product with water to provide (1-cyanocyclohexyl)acetic acid benzyl ester of the formula:

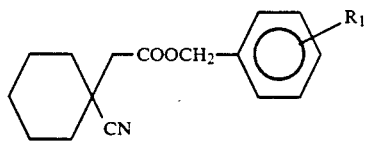

wherein $R_1$ is defined as above; and (b) hydrogenating the (1-cyanocyclohexyl)acetic acid benzyl ester in the presence of a hydrogenating catalyst with hydrogen to form the 1-(aminomethyl)cyclohexane acetic acid.

2. Process according to claim 1, wherein hydrogen chloride, hydrogen bromide or anhydrous sulfuric acid is used as the mineral acid.

3. Process according to claim 1, wherein the reaction is performed at a pressure between 1 and 10 bars and at temperatures between $-20°$ and $50°$ C.

4. Process according to claim 1, wherein the reaction is performed in the presence of a solvent.

5. Process according to claim 1, wherein the hydrolysis takes place with water at temperatures between $-20°$ and $100°$ C.

6. Process according to claim 2, wherein the reaction is performed at a pressure between 1 and 10 bars and at temperatures between $-20°$ and $50°$ C.

7. Process according to claim 6, wherein the reaction is performed in the presence of a solvent.

8. Process according to claim 7, wherein the hydrolysis takes place with water at temperatures between $-20°$ and $100°$ C.

9. Process according to claim 1 wherein a platinum, palladium, ruthenium, rhodium catalyst, optionally applied to an inert support, a Raney catalyst or a metal oxide is used as the hydrogenating catalyst.

10. Process according to claim 9 wherein the catalyst is used in amounts of 1 to 50 percent by weight, relative to the (1-cyanocyclohexyl)acetic acid benzyl ester.

11. Process according to claim 9 wherein the hydrogenation is performed at a pressure between 1 and 100 bars and at a temperature between $0°$ and $100°$ C.

12. Process according to claim 9 wherein the hydrogenation is performed in the presence of a solvent.

13. Process according to claim 10 wherein the hydrogenation is performed at a pressure between 1 and 100 bars and at a temperature between $0°$ and $100°$ C.

14. Process according to claim 13 wherein the hydrogenation is performed in the presence of a solvent.

* * * * *